United States Patent [19]

Fangrow, Jr.

[11] Patent Number: 4,898,174

[45] Date of Patent: Feb. 6, 1990

[54] AUTOMATIC VENTILATOR

[75] Inventor: Thomas F. Fangrow, Jr., Corona, Calif.

[73] Assignee: Life Support Products, Inc., Irvine, Calif.

[21] Appl. No.: 189,652

[22] Filed: May 3, 1988

[51] Int. Cl.⁴ .................. A62B 7/00; A61M 16/00
[52] U.S. Cl. ................... 128/204.24; 128/204.26; 128/205.24
[58] Field of Search ............... 128/204.18, 204.21, 128/204.23, 205.24, 205.23, 204.24, 204.26

[56] References Cited

U.S. PATENT DOCUMENTS

| | | | |
|---|---|---|---|
| 2,774,346 | 12/1956 | Halliburton | 137/101.11 |
| 3,189,027 | 6/1965 | Bartlett, Jr. | 128/205.24 |
| 3,267,935 | 8/1966 | Andreasen et al. | 128/204.23 |
| 3,795,257 | 3/1974 | Fabish et al. | 128/204.26 |
| 4,141,356 | 2/1979 | Smargiassi | 128/204.23 |
| 4,211,221 | 7/1980 | Schwanbom et al. | 128/204.18 |
| 4,227,519 | 10/1980 | Warnow et al. | 128/205.24 |
| 4,281,651 | 8/1981 | Cox | 128/204.23 |
| 4,340,045 | 7/1982 | Manley | 128/204.24 |
| 4,421,113 | 12/1983 | Gedeon et al. | 128/204.23 |
| 4,437,461 | 3/1984 | Greenberg | 128/205.24 |
| 4,459,982 | 7/1984 | Fry | 128/204.23 |
| 4,466,433 | 8/1984 | Robbins | 128/205.24 |
| 4,493,339 | 1/1985 | Porter, Jr. | 128/205.24 |
| 4,501,293 | 2/1985 | Furlong et al. | 128/205.23 |

FOREIGN PATENT DOCUMENTS

| | | | |
|---|---|---|---|
| 2233991 | 2/1973 | Fed. Rep. of Germany | 128/205.23 |
| 2162429 | 2/1986 | United Kingdom | 128/204.18 |

Primary Examiner—Edgar S. Burr
Assistant Examiner—Kimberly L. Asher
Attorney, Agent, or Firm—Knobbe, Martens, Olson & Bear

[57] ABSTRACT

A patient demand valve is automatically cycled open to provide selected volumes of oxygen at selected intervals. A pneumatic controller connected to an oxygen supply provides a control pressure to operate the demand valve, with the cycling provided by pneumatic timers. The oxygen supply to the patient is also through the controller to the demand valve. A tidal volume flow control valve provides an adjustable flow rate when open. In one embodiment, the patient demand valve is in an assembly which includes a safety subassembly, which incorporates a signaling device that indicates an over-pressure condition in the assembly as a result of a blockage of gas flow to the patient, and also includes an anti-suffocation valve.

47 Claims, 9 Drawing Sheets

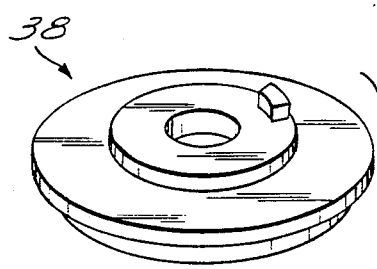
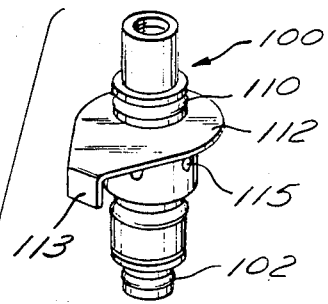
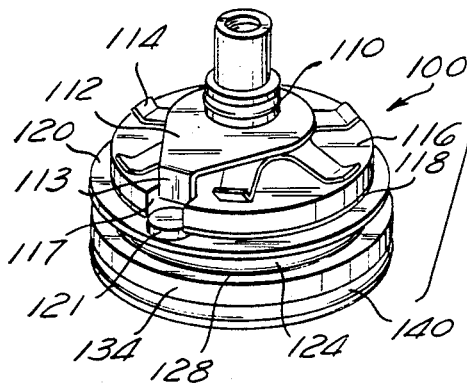
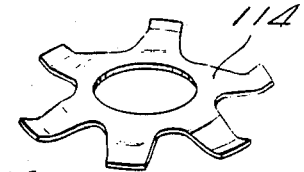
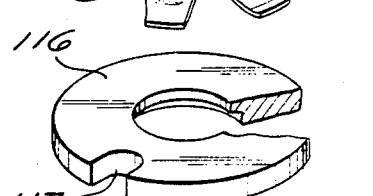
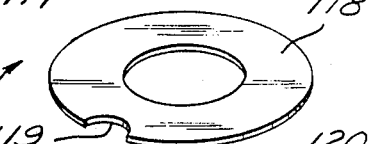
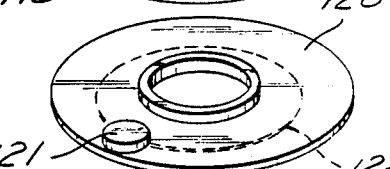
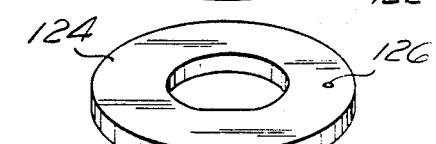
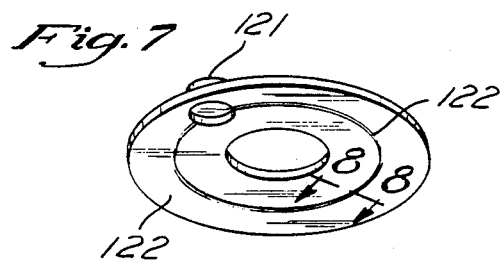
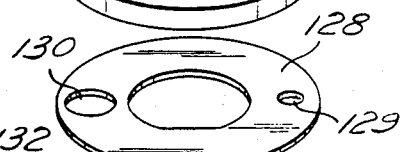
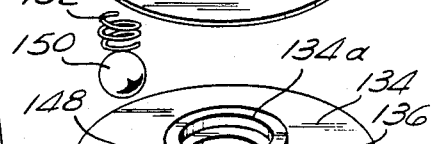
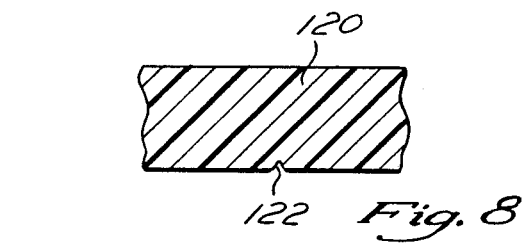
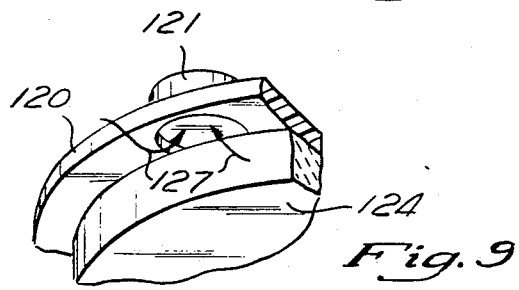
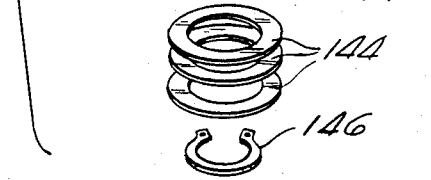

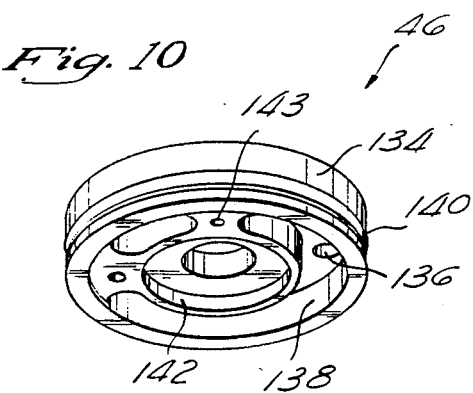
Fig. 10
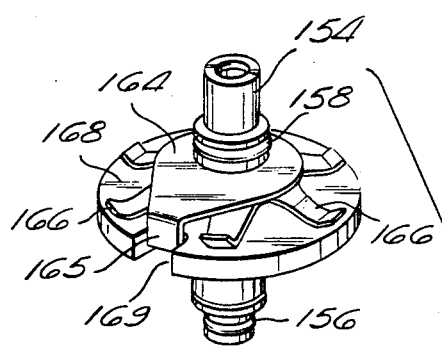
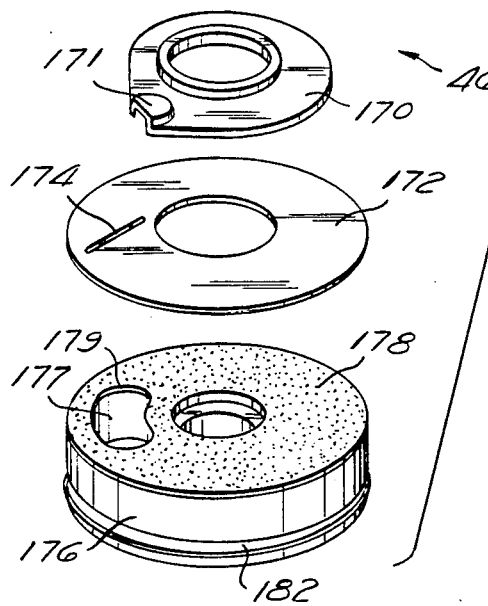
Fig. 12
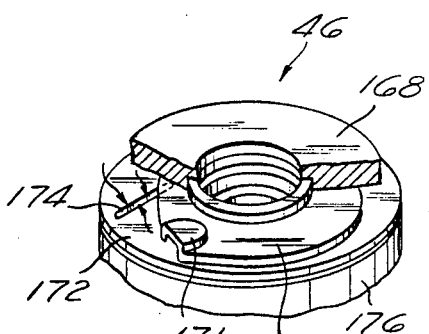
Fig. 13

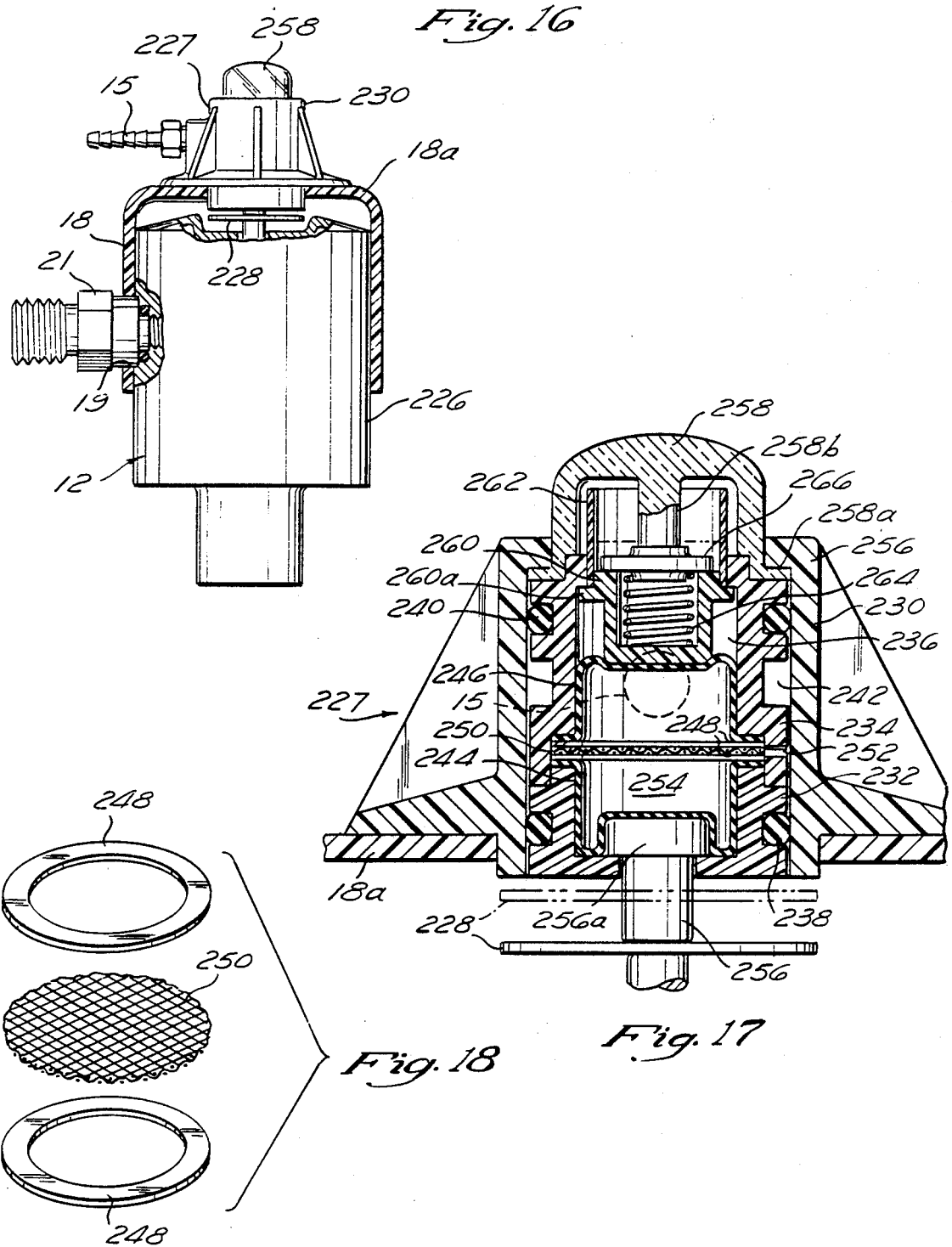

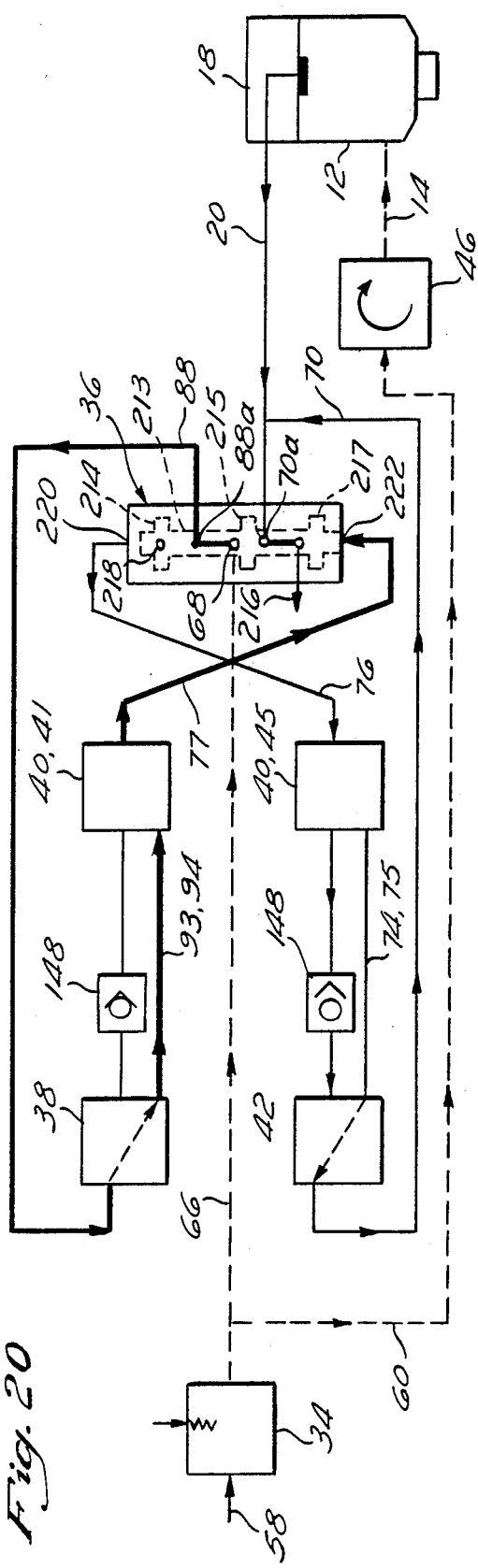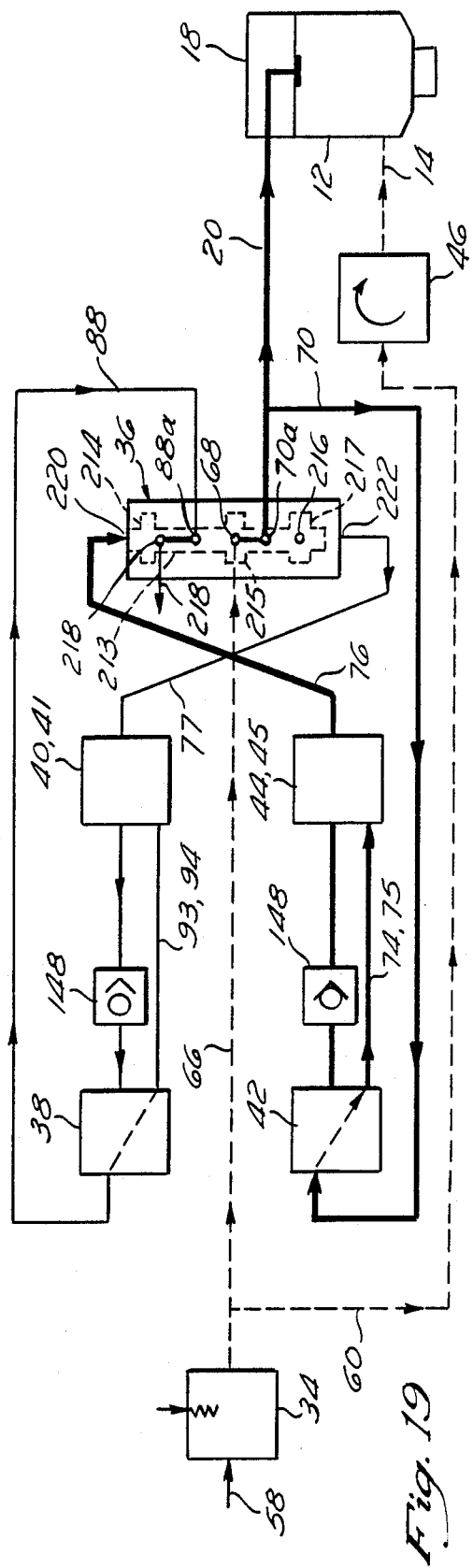

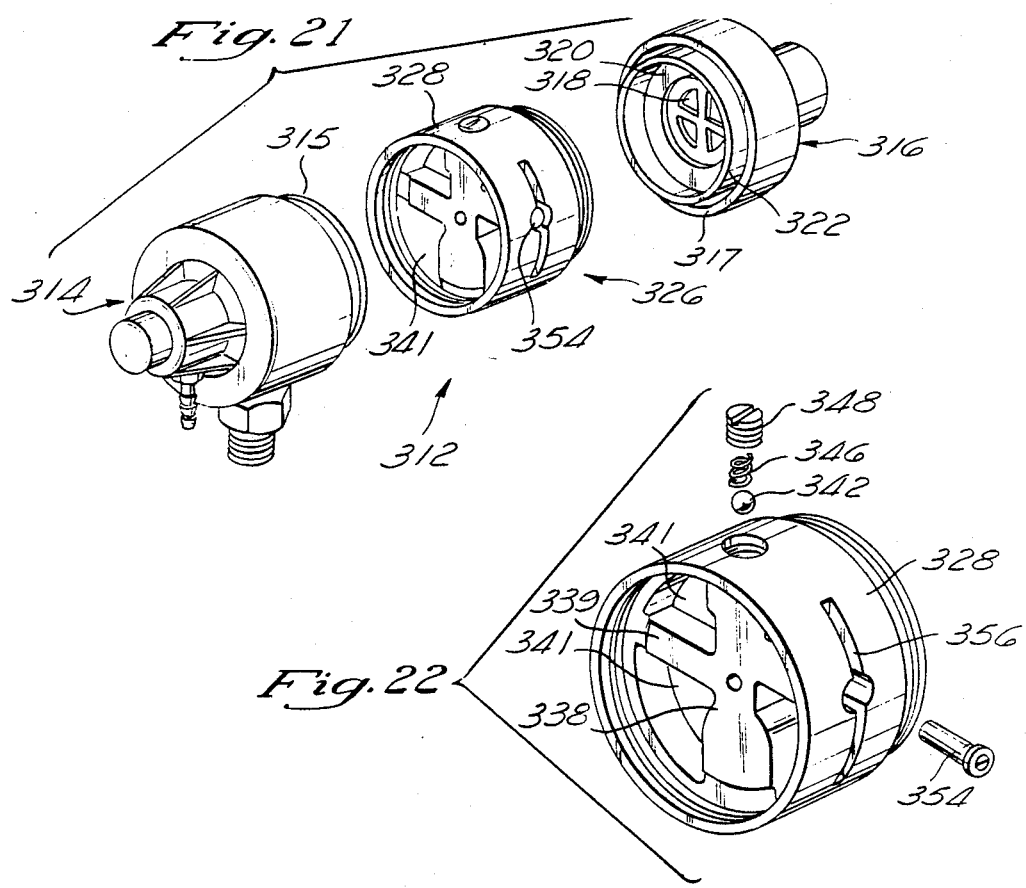
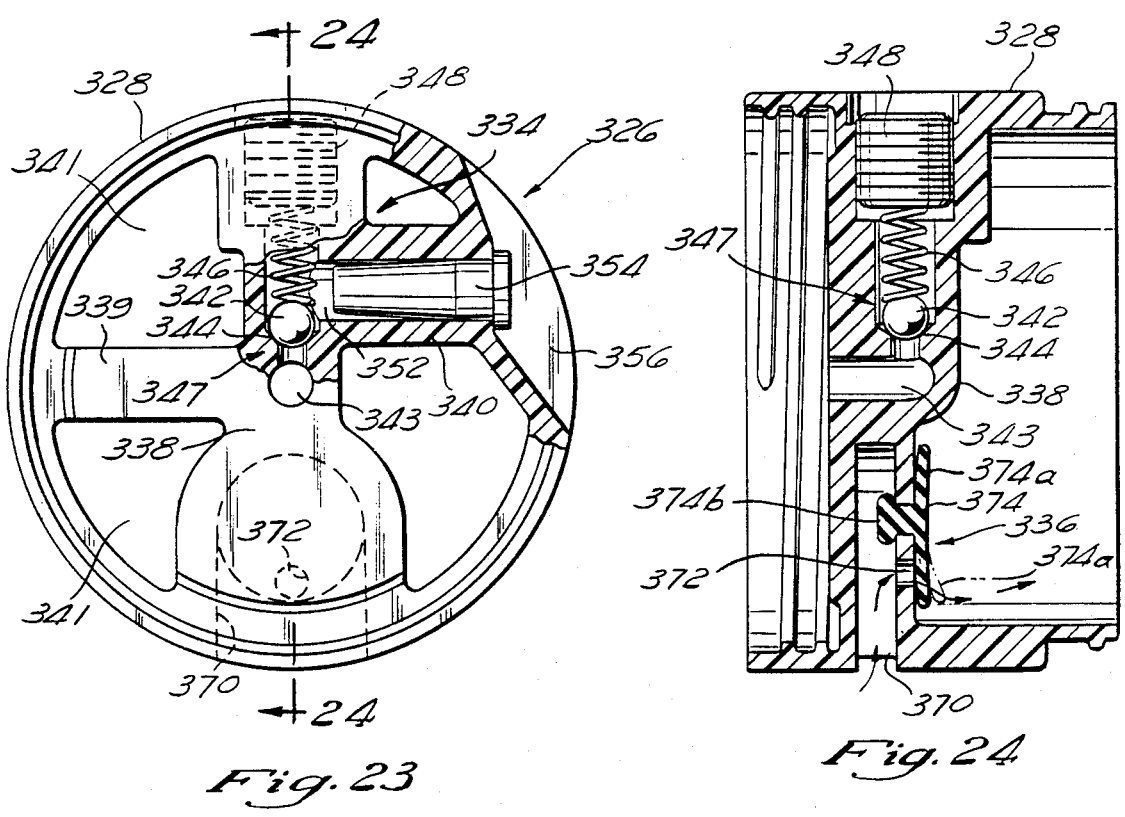

AUTOMATIC VENTILATOR

Field of the Invention

This invention relates generally to gas flow regulates devices, and more specifically to lung ventilation and resuscitation devices used in combination with a patient demand valve assembly.

Background of the Invention

Demand valve resuscitators are widely used to revive a non-breathing patient. An inlet side of the device is connected to a source of pressurized gas such as oxygen, and the outlet is connected to a patient by suitable means such as a mask. If the patient is not breathing, the attendant actuates an element to cause oxygen to be supplied to the patient. The resuscitator includes an exhaust valve that permits the patient to exhale directly through the mask. When the patient starts to breathe, the inhale pressure reduction created by the patient is sufficient to open a pilot valve which then opens a main valve such that the oxygen is supplied on demand. While the patient is not breathing, the attendant typically manually cycles the opening and closing of the resuscitator pilot and main valves to provide periodic flow of oxygen to the patient, while providing OFF intervals for exhalation through the device. Although there are several valves in an assembly of this type, the device is often simply referred to as a "demand valve."

Manual cycling of the demand valve in this fashion requires operator skill and attention to make sure that the amount of oxygen supplied for the particular patient is appropriate and that the intervals in which oxygen is supplied is also appropriate. Many attendants are not sufficiently skillful and experienced to consistently handle that function properly for the wide variety of patients treated in a wide variety of circumstances. Further, while oxygen input intervals can be manually timed, the operator must concentrate on that function to have proper manual cycling of the valve, and it is difficult for the operator to focus on other activities that should be accomplished or observed. The difficulty of the operation is also compounded by the fact that the demand valve is usually being operated in an emergency situation such that proper attention and concentration to the timing and cycling of the demand valve is difficult.

Automatic ventilation equipment used with a patient valve other than a demand valve has been available for some time. The American Medical Association had initially taken the position that, while performing cardiac pulmonary resuscitation (CPR), automatic ventilators should not be used; however, this recently changed such that there is an increased need for automatic ventilators. Patient demand valves have many advantages, and many of such devices are in use. Accordingly, a need exists for a convenient and practical automatic ventilator which will work in cooperation with a demand valve, including existing demand regulator valves. Further, it is desirable that the ventilator controls be combined in a single, easy to operate module. It is also desirable that the tidal volume of gas supplied to the patient be adjustable, and that frequency or intervals for providing breathable gas be adjustable. It is also desirable that the ventilator controller be connected to an existing high pressure gas supply, and that the controller be the only connection to the demand valve.

SUMMARY OF THE INVENTION

Briefly stated, there is provided an automatic ventilator system for providing desired volumes of oxygen or other gas to a patient at desired intervals. The system includes a pneumatic controller operating a patient demand valve by means other than in response to the patient's breathing, to provide automatically a measured quantity of gas to the patient at desired intervals. The supply of oxygen to the demand valve is preferably through the controller. Also, the controller provides an output control pressure which is applied to an actuator on the demand valve to open the demand valve at desired intervals for a desired period of time. This function is accomplished entirely pneumatically utilizing the pressurized breathable gas supply which is available for the patient.

The controller includes a pneumatic timer to measure the period of time in which the control pressure is applied to the demand valve, and thus, in combination with a tidal volume control valve, determines the volume of gas supplied while the demand valve is open. A second pneumatic timer controls the period of time that the control line pressure is not applied to the demand valve, whereby this off-timer controls the intervals between the on periods. In other words, it controls the frequency at which a desired volume of gas is applied to the patient. This off-timer is preferably adjustable to fit the needs of a wide variety of patients in a wide variety of circumstances.

Each of the pneumatic timers includes a flow control valve and a timing chamber in which gas is accumulated until predetermined pressures exist in the chambers. These pressures are applied to a slidable spool within a multiport shuttle valve. When the control pressure is being applied through a control pressure line to the demand valve to open the demand valve, that same control pressure is applied through the on-timer flow control valve to the on-timer chamber. When the pressure in that chamber reaches a certain level, that pressure causes the shuttle valve to vent the control line so that the demand valve closes, and also vents the on-timer chamber. Further, control gas is then applied to the flow control valve in the off-timer, and hence to the off-timer chamber which is in communication with the shuttle valve spool. After a predetermined interval, the pressure in the off-timer chamber causes the shuttle valve to once again switch to the on position, causing control pressure to be applied to the demand valve and also causing the off-timer chamber to vent.

The various controller components are provided in a single compact housing with the flow passages between the components integrally formed in the housing. The two timer flow control valves and the tidal volume control valve are positioned in a row diagonally across a rectangular housing to minimize the size of the controller module while maximizing the space available for manually operable knobs for adjusting those valves. An input line pressure regulator and the shuttle valve are also compactly positioned within the control module, arranged in a manner such that the oxygen input line is on one end of the module, and the oxygen supply line and control line to the demand valve exit from the opposite side of the module.

The downstream end of the control line pressure is connected to a shell which fits over the end of the demand valve. The control line pressure actuates a piston which depresses the manually operated button of a conventional demand valve to open the valve. The control line pressure also operates a movable indicator in the shell which indicates when oxygen is being supplied to the patient.

As a further feature of the invention, the patient demand valve has been modified to incorporate a signaling device to warn the operator of the automatic ventilator that the patient is not receiving the desired oxygen flow. This might occur, for example, if the patient's windpipe is blocked. The consequence of such blockage would be that the incoming pressure in the patient demand valve rises. This increased pressure is utilized to provide an audible sound to signal the operator. Preferably, a check valve opens at a predetermined level, allowing pressure to be relieved and the excess oxygen to flow through a sound producing element.

As another feature of the modification to the demand valve, there is provided an anti-suffocation valve which allows the patient to draw in external air if, for some reason, inadequate oxygen is obtained through the automatic ventilator. The modifications to the demand valve are incorporated into an assembly which fits within an existing demand valve structure between an upstream main valve and pilot valve subassembly and a downstream subassembly containing a valve to the patient and an exhale valve. Such an arrangement is advantageous in that these two features can be easily added to a large number of demand valves already in use and also added to newly manufactured demand valves without undergoing the cost of changing existing production equipment.

BRIEF DESCRIPTION OF THE DRAWINGS

FIG. 5 is an exploded perspective view of the off-timer flow control valve.

FIG. 6 is an exploded perspective view of the valve of FIG. 5.

FIG. 7 is a perspective view of a valve seat disc containing the flow passage of the valve of FIGS. 5 and 6.

FIG. 8 is an enlarged cross-sectional view of the disc of FIG. 7 on line 8—8.

FIG. 9 is a fragmentary, enlarged perspective view of a portion of the valve of FIGS. 5 and 6.

FIG. 10 is a bottom perspective view of the main valve body of FIGS. 5 and 6.

FIG. 12 is an exploded perspective view of the tidal volume flow control valve.

FIG. 13 is an assembled, partially sectionalized view of the valve of FIG. 12.

FIG. 16 is a partially sectionalized view of the shell mounted on the demand valve.

FIG. 17 is a cross-sectional view of the actuator for pneumatically operating the demand valve.

FIG. 18 is an exploded perspective view of the inlet to the actuating diaphragm of FIG. 17.

FIG. 19 is a schematic view illustrating operation of the system when oxygen is being supplied to the patient.

FIG. 20 is a schematic view illustrating operation of the system when measuring intervals between supplying oxygen to the patient.

FIG. 21 is an exploded perspective view of a patient demand valve with a separate safety subassembly including an over pressure alarm and an anti-suffocation valve.

FIG. 22 is an exploded perspective view of the safety subassembly of FIG. 21.

FIG. 23 is an end elevational view of the safety subassembly of FIG. 21, with a portion of the structure in cross section.

FIG. 24 is a cross-sectional view on line 24—24 of FIG. 23.

DETAILED DESCRIPTION OF A PREFERRED EMBODIMENT

Figure 1:
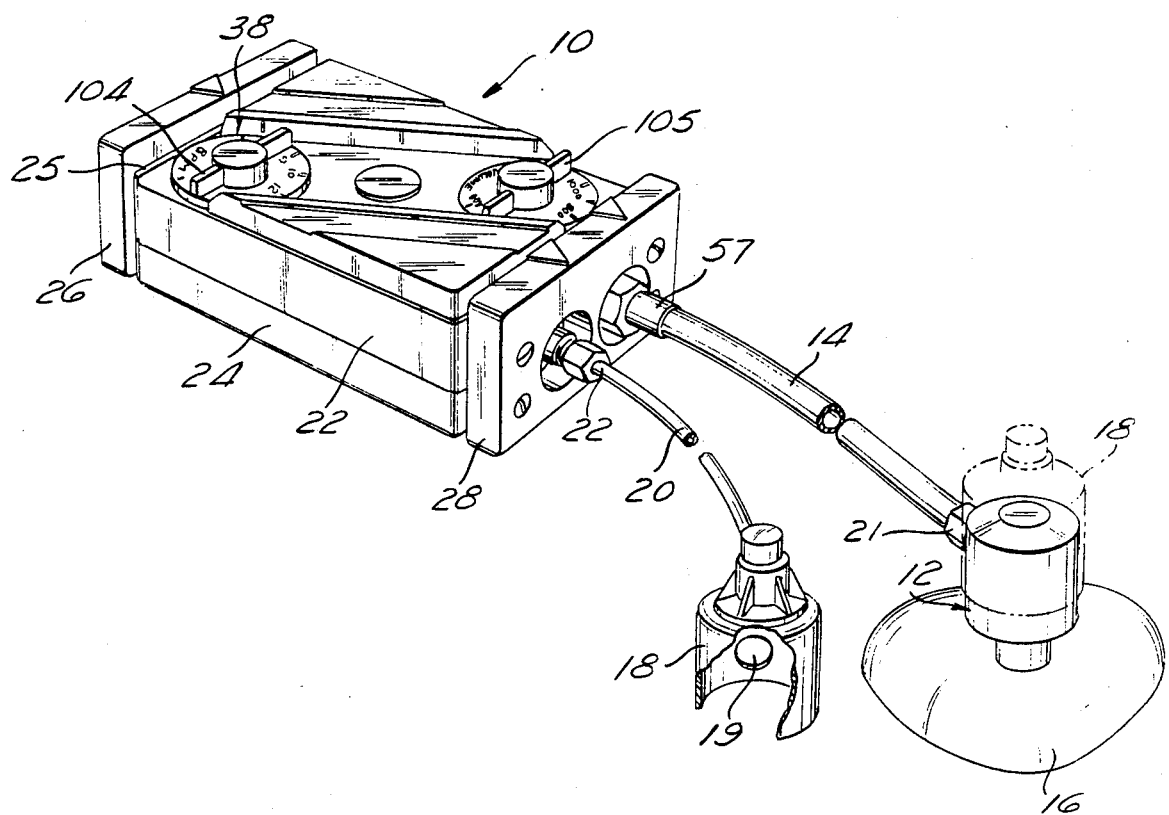
FIG. 1 is a perspective view of the automatic ventilator system of the invention.

Referring to FIG. 1, there is illustrated an automatic ventilator controller or control module 10, a patient demand valve resuscitator 12 connected to the controller by a flexible oxygen supply line 14 and connected to a patient face mask 16. Also illustrated is a control shell 18 connected to the control module 10 by a flexible control line 20. The shell 18 fits onto the demand valve assembly 12 as is illustrated in broken lines in FIG. 1. The control shell 18 has a cylindrical side wall that fits over the demand valve assembly 12 and includes an opening 19 through which the supply line 14 extends when the shell is positioned on the demand valve.

The control module includes a housing formed by an upper shell-like section 22 which mates with a lower section 24. The operating components of the controller are confined within that housing. The housing sections 22, 24 are held together by a pair of rectangular frames, one of which is shown at 25 in FIG. 1. These frames fit over projecting portions (not shown) on the sections 22, 24. These frames are held in position by an input end rubber bumper 26 and an output end rubber bumper 28 attached by suitable fasteners to the housing sections.

Figure 2:
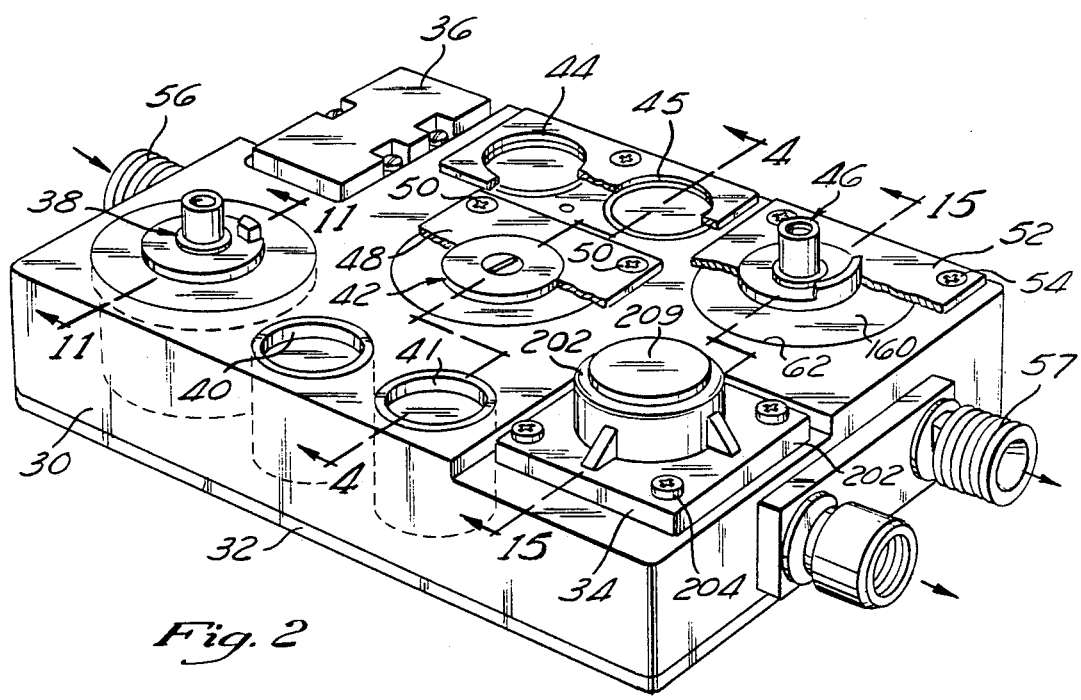
FIG. 2 is a perspective view of the ventilator control module.
Figure 3:
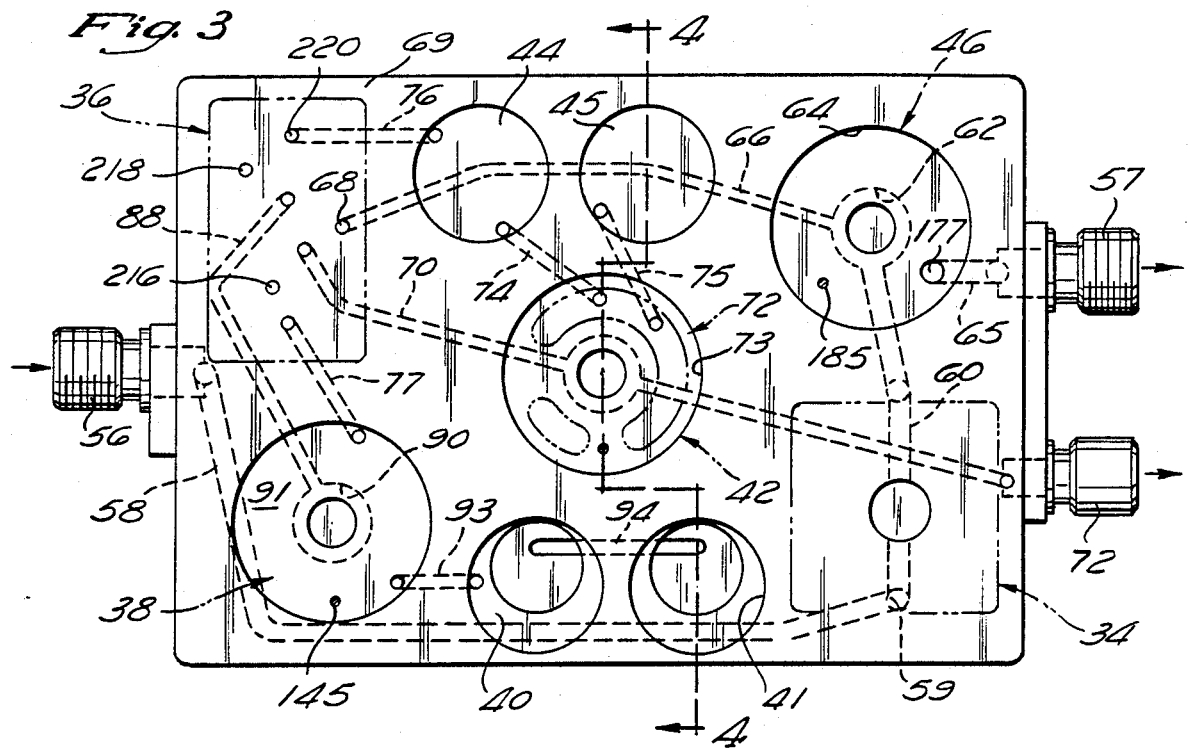
FIG. 3 is a somewhat schematic view of the module illustrating the gas flow passages within the module housing.

Within the controller module housing, there is positioned a rectangular plastic block 30, as shown in FIG. 2. This block has a series of sockets or compartments formed therein which open to the upper surface of the block. The lower ends of these compartments are interconnected by a plurality of flow passages which are formed integrally in the bottom surface of the plastic block, as best seen in FIG. 3. These passages are closed by a bottom plate 32, shown in FIG. 2. It should be noted that the block of FIG. 2 is a machined prototype, and, in production, the block will be molded having various recesses between interconnected walls forming the sockets and compartments, all in accordance with good molding practice regarding wall thickness, etc.

Within the sockets or compartments in the upper portion of the block 30 are positioned the various control components of the module. This includes a pressure regulator 34, a spool or shuttle valve 36, an off-timer flow control valve 38, an off-timer chamber in the form of a pair of chambers 40, 41, an on-timer flow control valve 42, an on-timer chamber in the form of a pair of chambers 44, 45, and a tidal volume flow control valve 46. The individual compartments or chambers formed in the block 30 are each separately closed by an upper plate attached by screws or other simple fastening means to the upper surface of the block. Thus, for example, a closure plate 48 is shown attached by screws 50 to close the chamber in which the on-timer flow control valve 42 is positioned. Similarly, a plate 52 is shown attached to the block by suitable fasteners 54 covering the upper end of the compartment in which the tidal volume valve 46 is positioned. Utilizing individual plates simplifies operation in the event a single component needs to be inspected or replaced.

Referring to FIGS. 2 and 3, a gas inlet fitting 56 is shown mounted in the wall of the block 30. An elongated passage 58 formed in the lower portion of the block directs the inlet gas to an inlet passage 59 in the block to the pressure regulator 34 which is positioned on the other side of the block. A suitable air filter (not shown) may be conveniently positioned in the passage 59 through a hole (not shown) in the side of the block 30. A regulated outlet pressure passage 60 extends from the regulator 34 to an annular passage 62 beneath the socket or chamber 64 for the tidal volume flow control valve 46. An elongated passage 66 extends from the annular passage 62 to an inlet opening 68 in the bottom wall 69 which receives the spool valve or shuttle valve 36.

An elongated passage 70 extends from an outlet in the spool valve, beneath the pressure regulator chamber to outlet 72, leading to the flow control line 20. The passage 70 also extends beneath the chamber 73 for the on-timer flow control valve such that the control pressure from the spool valve is also applied to that flow control valve. The on chamber 73 is further connected by passages 74, 75 to the two on-timer chambers 44, 45. These chambers are in turn connected by sensing pressure passage 76 to one end of the shuttle valve 36.

A passage 88 interconnects another outlet from the shuttle valve to annular passage 90 beneath the chamber 91 for the off-timer flow control valve. The chamber 91 is in turn connected by passages 93, 94 to the off-timer chambers 40, 41. The chamber 91 is also connected by sensing passage 77 to the end of the shuttle valve opposite from the sensing passage 76 leading to the on-timer chambers.

Figure 4:
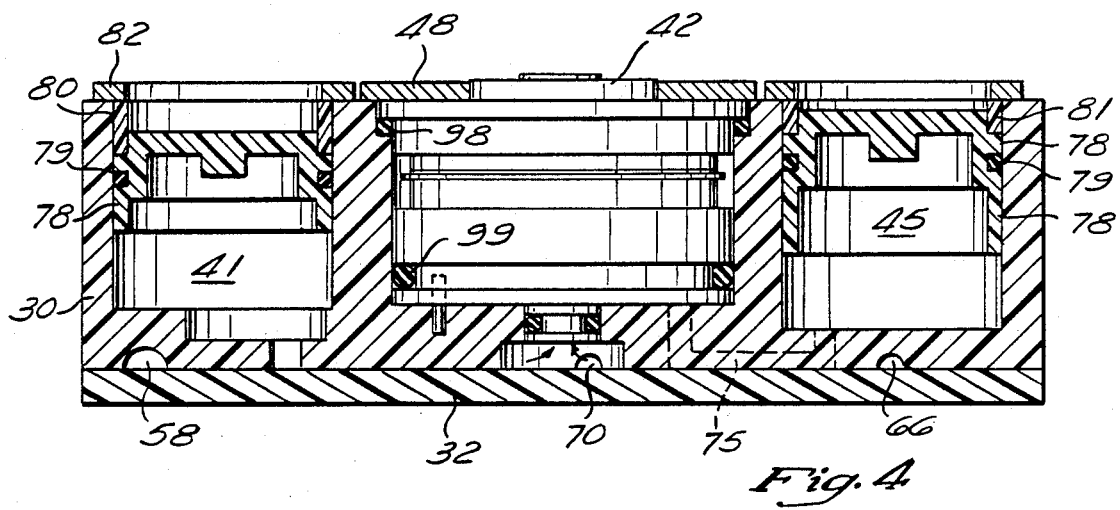
FIG. 4 is a cross-sectional view on line 4—4 of FIG. 2 illustrating the timer chambers and the timer flow control valve.
Figure 4A:
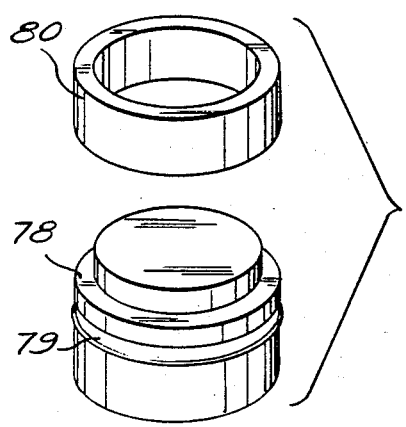
FIG. 4a is an exploded perspective view illustrating a portion of the timer chamber.

Referring to FIGS. 4 and 4a, the off-timer chamber 41 includes an inverted cup-shaped member 78 carrying an 0-ring 79 which is slidably mounted in the chamber 41. A spacer ring 80 extends between the cup-shaped member 78 and an upper retaining plate 82. By utilizing spacer rings 80 of different axial height, the volume of the chambers may be conveniently selected to control volume, which in turn controls the time of filling the chamber. The on-timer chamber 45 in FIG. 4 is shown with an axially shorter spacer ring 81 such that its volume is greater than that illustrated for the off-timer chamber 41.

Timer Flow Control Valves

FIG. 4 also illustrates the on-timer flow control valve 42 positioned within its socket 73 together with a pair of sealing 0-rings 98, 99. The on-timer flow control valve has the same internal construction as the off-timer flow control valve 38. The details of this construction is illustrated in FIGS. 5–11 for valve 38.

This flow control valve construction includes a tubular core 100 which is open on its lower end to serve as a gas inlet. The lower end of the core 100 fits within a mating bore in the block 30. An 0-ring 102 captured in an annular groove on the lower end of the core seals the lower exterior of the core in that area, with the core being free to rotate within the block. The upper end of the valve core 100 extends out of the block and has threadably mounted thereon manual control knob 104, FIG. 1. The upper end of the valve chamber is closed by a cover 106 with an 0-ring 108 compressed between the block and a flange on the cap, and with the cap being held in position by a plate 49, similar to plate 48 in FIG. 2. An 0-ring 110 on the valve core 100 seals the upper end of the core with respect to the cap 106.

A stack of components positioned on the tubular valve core includes a torque transmitter 112 fixed to rotate with the core 100, an axial spider-type spring 114 and a torque transmitter disk 116 having a notch 117 in its outer periphery which receives a depending finger 113 of the torque transmitter 112. Radial passages 115 connect the interior of the core to the space between the spring 114 and the disk, and hence to the upper end of the chamber 91. A thin washer 118 positioned beneath the disk 116 includes a notch 119 in its periphery aligned with the notch 117. The washer 118 distributes spring force to a valve seat disk 120 having an upwardly extending projection 121 adjacent its periphery and extending upwardly through the notches 119, 117. The projection 121 is hollow and opens into the lower face of the valve seat disk 120. A fine flow passage groove 122 is formed in the lower surface of the valve seat disk 120 in the form of a ring which intersects the open end of the projection 121, as best seen in FIGS. 6, 7 and 8.

Figure 11:
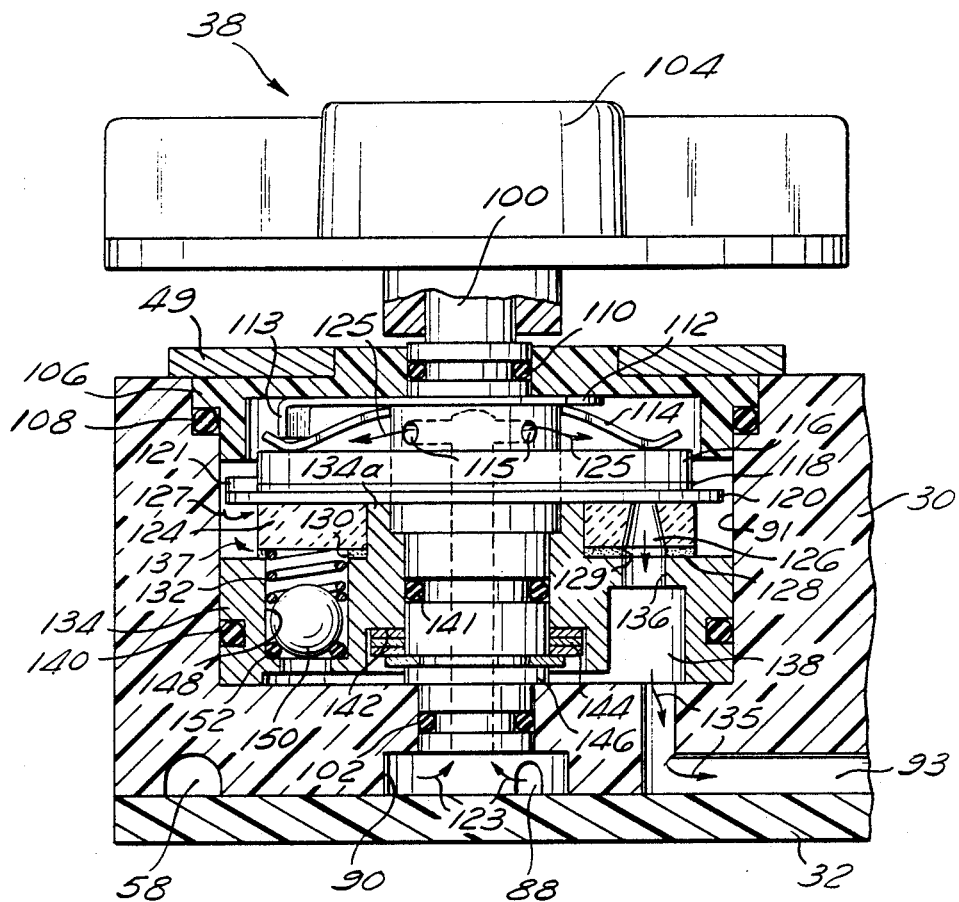
FIG. 11 is a cross-sectional view of the off-timer flow control valve on line 11—11 of FIG. 2.

A ring-shaped flow passage disk 124 is positioned beneath the valve seat disk 120 and includes a hole 126 which is spaced outwardly from the center of the disk aligned with the groove 122 in the valve seat disk. A sealing washer 128 is located below the disk 124 and includes a hole 129 which is aligned with the hole 126, and includes a hole 130 for receiving a check valve spring 132. A disk-shaped valve body 134 is positioned beneath the washer 128 and includes an axial projection 134a which extends through the washer 128 and the disk 124. The exterior of this projection includes a flat portion 134b which mates with a central opening in the disk 124 and the washer 128 so that those components are fixed with respect to the valve body 134 and do not rotate with the valve core 100. A hole 136 spaced outwardly from the center of the valve body 134 is aligned with the holes 129, 126 to continue the flow passage. Also, the hole 136 opens to an arcuate recess 138 formed in the lower face of the valve body, as best seen in FIG. 10. An 0-ring 140 positioned within a groove in the periphery of the valve body 134 seals the exterior of the valve body with respect to the surrounding block 30, as seen in FIG. 11. The interior bore of the valve body 134 is formed with a shoulder that receives a conforming portion of the valve core 100. An 0-ring 141 positioned on the valve core slides within the valve body bore to seal the valve body with respect to the core in that area (see FIG. 11). The lower face of the valve body 134 has a central recess 142 (see FIG. 10) in which is positioned a stack of spacing washers 144 and a retaining snap ring 146 which axially holds the various components on the valve core.

Also shown in FIG. 10 is a positioning hole 143 in the lower surface of body 134 which is adapted to receive a positioning pin 145, shown in the chamber 91 in FIG. 3. The pin positions the valve and prevents the valve from rotating.

Formed in the upper surface of the valve body 134 is a socket 148 spaced outwardly from the center of the valve body and positioned generally diametrically opposite from the hole 136. This socket is also open to the lower face of the valve body and contains a check valve ball 150 which is urged downwardly by the spring 132 against an 0-ring type valve seat 152 positioned on a shoulder in the lower end of the socket 148.

In operation of the off-timer flow control valve 38, gas from the shuttle valve 36 flows through the passage 88 into a recess 90 in the lower end of the block 30 beneath the valve core 100. As illustrated by the arrow 123 in FIG. 11, the gas flows upwardly through the hollow valve core and out through the radial passages 115 near the upper end of the valve core, as seen by arrow 125. The gas then flows around the outer periphery of the valve seat disk 120 and into the open end the projection 121, as seen by arrow 127 in FIGS. 9 and 11. Note that the diameter of the valve seat 120 is greater than the diameter of the disk 124 such that the open end of the projection 121 is open to the gas flow.

Looking at FIGS. 7 and 11, it is seen that the open projection is in communication with the small groove 122 which intersects the hole 126 in the disk 124, as shown by arrow 123. That hole is axially open to the hole 129 in washer 128, and the hole 136 which opens into the arcuate passage 138 in the main valve body 134. The gas is then open to the passage 93, as seen by a row 135, leading to the off-timer chambers 40, 41.

It should be noted that the gas could not flow through the check valve 150 in that it is biased into a closed position by the spring 132. Thus, the timing is controlled by the small groove 122. However, when the shuttle valve is moved to a vent position such that the passage 88 is open to a vent, the flow reverses from that shown by the arrow 135, so that the gas in the timer chambers 40, 41 flowing into the arcuate recess 138 is dissipated quickly through the check valve 150, as shown by the arrow 137, rather than slowly through the small groove 122. The gas then flows radially inwardly, opposite from the arrow 125 through the passages 115 and downwardly through the core 100 to the passage 88, opposite to the arrow 123.

Tidal Volume Control Valve

Referring to FIGS. 12–15, the tidal volume control valve 46 is similar to the control valves 38 and 42 in that it includes a stack of components mounted on a central tubular core 154. The core is open on its lower end to the flow passage 60. The lower end of the core exterior is sealed with respect to the block 30 by means of an 0-ring 156 mounted in an annular groove on the core. Similarly, the exterior of the upper end of the core is sealed by an 0-ring 158 with respect to a cap 160 which closes the upper end of the chamber 64, seen in FIG. 3. An additional 0-ring 162 is compressed between a flange on the cap and a mating shoulder in the block. The plate 52 clamps the cap in position.

A torque transmitter 164 is positioned near the upper end of the core directly beneath the cap 160. This transmitter is mounted to rotate with the core and includes a depending finger 165 which fits between the fingers of a spider-like axial spring 166 and into a notch 169 in a disk 168. A ring-shaped movable valve element 170 is positioned beneath the disk 168 and includes an upwardly extending projection 171 which fits within the notch 169 in the disk. A ring-shaped valve seat 172 positioned beneath the valve element 170 has a valve orifice 174 in the form of a slot extending across the valve seat 172 in a non-radial orientation.

Figure 14:
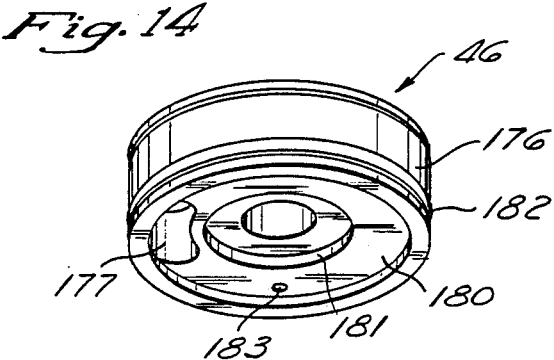
FIG. 14 is a bottom perspective view of the valve of FIG. 13.

The valve seat 172 is attached to the upper surface of a disk-shaped valve body by means of a two-sided disk-shaped sticky pad 178 having an arcuate opening 179, which is aligned with the slot 174. As seen from FIGS. 12 and 14, the valve body 176 includes an arcuate opening 177 aligned with the opening 179 in the pad 178. The opening 177 opens into a shallow recess 180 in the lower end of the valve body 176. A further smaller diameter annular recess 181 is centrally positioned within the recess 180. Also shown in FIG. 14 is a hole 183 which receives positioning pin 185 shown in FIG. 3. The valve body 176 is fixed with respect to the block 30 and is sealed with respect to the block by means of an 0-ring 182 positioned within an outer groove of the valve body. The valve core 154 is rotatably mounted within the bore of the valve body 176 and includes an 0-ring 184 on the exterior of the valve core to seal the valve core in that area. A shoulder 154a formed on the valve core 154 fits within a recess in the upper end of the valve body. The various components stacked on the core 154 are secured thereto by a plurality of washers 186 and a retainer 188.

Figure 15:
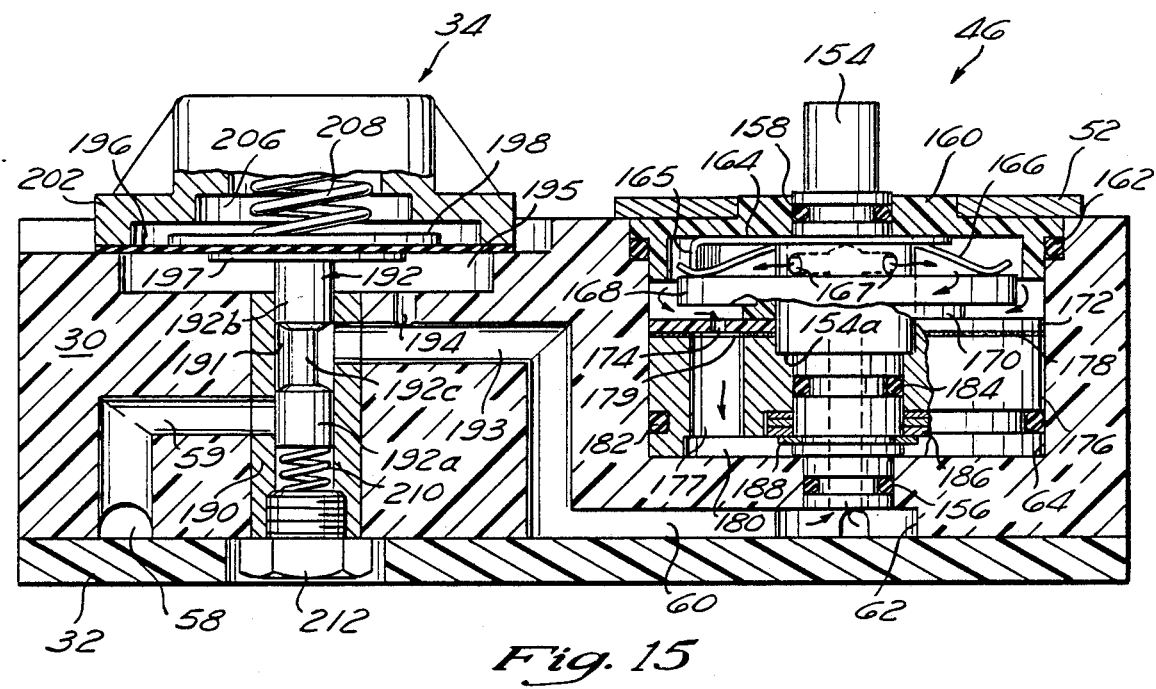
FIG. 15 is a cross-sectional view of the tidal volume flow control valve on line 15—15 of FIG. 2 and illustrating the control module pressure regulator.

As may be seen from FIG. 15, gas from the block passage 60 opens into the block annular recess 62 which is in communication with the open lower end of the core 154. Gas flows upwardly through the core and out the radially extending passages 167, between the spring 166 and the disk 168, around the outer periphery of the disk 168 and flows through the orifice 174 in the valve seat 172. The gas further flows downwardly through the opening 179 in the pad 178 and the opening 177 in the valve body. From there, it flows through a passage 65, as shown in FIG. 3, through the outlet fitting 57 to the gas supply line 14 leading to the demand valve 12.

Pressure Regulator

The pressure regulator 34 is basically a purchased component, schematically illustrated in FIG. 15 incorporated into the single module block 30. The regulator includes a sleeve 190 positioned within a bore in the block 30. A valve poppet 192, axially movable within the sleeve 190, includes an enlarged lower portion 192a and upper portion 192b joined by a smaller diameter central section 192c which defines an annular passage 191 between the upper and lower portions. The inlet passage 59 formed in the block is in communication with the gas inlet passage 58 and a hole in the sleeve 190 which opens into the annular passage 191, depending upon the axial position of the poppet. It should be understood that the sleeve and the poppet cooperate such that, with the poppet positioned as shown in FIG. 15, no flow occurs. An outlet passage 193 formed in the block also opens to the annular passage 191 and is aligned with a hole in the sleeve to form an outlet from the regulator. The outlet passage 193 is further connected by an orifice 194 to a diaphragm chamber 195 formed in the upper surface of the block 30. A flexible diaphragm 196 extends across this chamber 195 secured to a centrally located disk 197 on the upper end of the valve poppet and another disk 198 on the top side of the diaphragm. The diaphragm 196 is clamped to the upper surface of the block 30 by means of an upper cap 202 which is secured by suitable fasteners 204 to the block, as seen in FIG. 2. The cap includes an interior passage 206 in which is positioned a spring 208 which urges the diaphragm downwardly. The spring is positioned beneath a retainer button 209 in the upper end of the cap, as seen in FIG. 2. A spring 210 on the lower end of the poppet is captured within the sleeve and held in position by means of a bolt 212 extending through the bottom plate 32.

When the pressure on the outlet side of the regulator is low so that there is low pressure in the chamber 195 beneath the diaphragm, the upper spring 208 will force the poppet downwardly, causing flow through the regulator passage 191. As the pressure on the outlet side increases, this pressure in the diaphragm chamber 195 urges the diaphragm upwardly together with the poppet to reduce flow and outlet pressure. By adjusting the bolt 212 to vary the force provided on the poppet 192 by the spring 210, the desired output pressure may be obtained.

Shuttle Valve

The spool or shuttle valve 36, shown in FIG. 2, is a purchased component available from Kuhnke Pneumatics, 26 West Highland Avenue, Atlantic Highlands, New Jersey. As schematically shown in FIGS. 19 and 20, the shuttle valve includes a spool-shaped valve member 213 having a plurality of axially spaced lands 214, 215, 217 which cooperate with a plurality of openings leading to the spool. This includes an inlet 68, a pair of outlets 70a and 88a leading respectively to lines 70 and 88, a pair of vents 216 and 218, and openings 220 and 222 on opposite ends of the spool. In use, the shuttle is axially switched between on and off positions in accordance with the pressure sensed on the ends of the spool.

Demand Valve and Actuator

Referring now to FIGS. 16–18, the demand valve assembly 12 has been sold for many years by Life Support Products, Inc., the assignee of the present invention, and is described in detail in U.S. Pat. No. 3,795,257, which is incorporated herein by reference. The assembly has a generally cylindrical body 226 with a depressible button 228 shown in its upper end. The button is spring-biased upwardly, which is its closed position. If, in manual resuscitation, it is desired to apply oxygen to the patient, the button in normal use is depressed by an operator. In the present invention, a mechanism 227 is provided for mechanically depressing the button in accordance with a pneumatic control pressure provided by the controller 10.

The oxygen supply line 14 (FIG. 1) includes a fitting 21 on its downstream end which extends through the hole 19 in the shell 18 and threads into the side of the demand valve. The shell includes an end wall 18a which fits over the end wall of the demand valve. A small housing 230 having a generally cylindrical configuration is positioned within a hole in the end wall 18a with the major portion of the housing extending away from the shell. A lower generally cylindrical body member 232 is positioned in the lower portion of the housing and mates with an upper generally cylindrical body member 234 to define an interior cylindrical chamber 236. An O-ring 238 carried by the lower body member 232 and an O-ring 240 carried by the upper body member 234 define between them a sealed annular space 242. A control line fitting 15 mounted in the housing wall opens into this space.

Positioned within the cylindrical space within the upper and lower bodies are a pair of generally cup-shaped diaphragms 244 and 246 that open toward each other, with annular flanges of the diaphragms extending outwardly and being clamped between the upper and lower body members. Also positioned between the flanges are a pair of washers 248 and a circular screen 250, best seen in FIG. 18. A hole 252 through one side of the upper body member connects the exterior annular space 242 to the edge of the screen, which in turn communicates with a chamber 254 formed between the two diaphragms.

A small piston 256 is positioned in the lower body member 232 with the head 256a of the piston being captured within the body member and being engaged by the end wall of the lower diaphragm 244. The body of the piston extends axially through an opening in the lower body member 232 and engages the operating button 228 on the demand valve.

A transparent cap 258, captured within the upper end of the housing, includes an outwardly extending flange 258a positioned within the housing and a main body portion which protrudes upwardly from the housing. Within the space formed by the cap and the upper end of the upper body member 234, there is positioned a cup-shaped indicator piston 260 having an outwardly extending flange 260a which retains it within the upper body member. A cylindrical indicator 262 is attached to the upper end of the indicator piston. The lower end of the piston 260 engages the upper surface of the upper diaphragm 246. A compression spring 264 is positioned within the cup-shaped indicator piston and a spring retainer 266 engages the upper end of the spring and the upper end of the indicator piston 260. A central finger-like projection 258b is formed in the cap and engages the upper end of the spring retainer 266 to limit its upward movement.

When the necessary control pressure is applied through the control line 20 into the annular space 242, through the hole 252 in the upper body and through the screen 250 into the interior diaphragm chamber 254, the then-collapsed diaphragms are moved to the extended position shown in FIG. 17. The actuator piston 256 is moved to its lowermost position wherein it depresses the demand valve operating button 228 to open the demand valve. Simultaneously, the upper diaphragm 246 moves the indicator piston 260 and the cylindrical indicator 262 upwardly into the transparent cap 258. The presence of the indicator in the cap tells the operator that the patient is receiving oxygen through the demand valve. When the control line pressure is vented, the spring-biased demand valve button 228 pushes the actuator piston 256 upwardly, and the indicator spring 264 pushes the indicator piston 260 and the indicator 262 downwardly. The indicator not being visible in the transparent cap 258 tells the operator that oxygen is not being supplied to the patient.

Overall Operation

Refer now to FIGS. 19 and 20, as well as FIGS. 1, 2 and 3, for a discussion of the overall operation of the system. FIG. 19 schematically illustrates the operation of the system during inspiration, i.e., while oxygen is being supplied to the patient. The system is ON. The broken line indicates the regulated gas flow. The heavy solid line indicates the control line gas flow and pressure, and the light solid line indicates the gas flow to vent.

As seen, the input high pressure gas through fitting 56 of FIG. 3 flows through line 58 to the pressure regulator 34. One output from the regulator flows by line 60 directly to the tidal volume flow control valve 46 and then hence by passage 65 (FIG. 3) to the supply line 14 into the demand valve 12. The valve 46 has been adjusted open to a desired setting by the knob 105. Regulated gas flow is also provided through passage 66 to the spool valve inlet port 68. With the spool valve positioned as indicated in FIG. 19, control gas pressure is applied through passage 76 to the control line 20 and the actuator 227 on the top of the demand valve 12. This pressure operates the actuator 227, FIG. 17, to depress the button 228 on the demand valve such that oxygen from the tidal volume flow control valve 46 is allowed to flow through the demand valve 12 to the patient.

The control pressure from the spool valve 36 is also applied through the line 70 to the on-timer flow control valve 42 which permits flow in the manner described above to the timer chambers 44, 45. The pressure in these chambers is applied through passage 76 to the end of the spool valve such that when the pressure has attained a certain level, the spool valve will shift to its off position.

In a prototype version of the system, it is necessary for the pressure in the on-timer chambers to reach 8 psi to shift the shuttle valve 36. The time that it takes the pressure to reach that level is dependent on the time that it takes a small volume of gas to flow through the groove 122, shown in FIGS. 6, 7 and 8, to raise the pressure in the chambers 44, 45 to that level. This in turn is dependent upon the rotational position of that flow control valve 42. In a prototype form of the invention, this path was set relatively short such that 8 psi was obtained in about 1.5 seconds. The control pressure from the control valve 42 cannot flow through the check valve 148 to reach the timer chambers in that the check valve is not oriented to prevent flow in that direction. The flow control valve 42 can be adjusted as desired. In the form of the invention illustrated, the operator is not provided a knob to adjust this valve, but one can be provided if further operation choice is desired. Instead, the valve is adjusted at the factory or service center. The volume of oxygen provided through the valve 46 and the demand valve 12 during the 1.5-second interval is dependent on the setting of the tidal volume flow control valve. This volume in milliliters, or other suitable measurement, may be indicated adjacent the control knob 105.

While the control pressure is being applied to the on-timer, the off-timer chambers 40, 41 are being vented through the shuttle valve vent 218. Once the preselected pressure for the on-timer chambers 44, 45 is reached, the shuttle valve shifts to the condition shown in FIG. 20, which is the expiration or demand valve OFF position. The control line 20 pressure of FIG. 19 has been shifted to the vent or dump position through vent 216. The venting of control line pressure immediately allows the demand valve button 228 to move to its normally OFF position, interrupting oxygen flow to the patient. Simultaneously, the control pressure in the on-timer chambers 44, 45 is vented quickly through the check valve 148 within the on-timer flow control valve 42 to the vent 216 in the spool valve. Note that the check valve 148 enables the flow to bypass the small groove 122 in valve 42 so that the venting is very quick.

The control output pressure from the spool valve 36 is directed through the line 88 to the off-timer flow control valve 38. The gas flows through its small groove 122 to the off-timer chambers 40, 41 by way of the passages 93, 94. The pressure from these chambers is also sensed by the line 77 on the lower end of the shuttle valve. Again, the time in which the flow to the patient is to be interrupted is dependent on the time that it takes to attain a preselected pressure in the off-timer chambers 40, 41. This, in effect, determines the frequency of the breaths or flow of oxygen to the patient, i.e., breaths per minute. The off-timer flow control valve is also adjustable, and it is provided with a manually-controlled knob 104, as seen in FIGS. 1 and 11.

Typically, the time that the gas flow to the patient is interrupted is a longer period of time than that in which the gas is being provided. For example, the flow control valve knob may be set so as to require about 6 seconds to reach the necessary pressure for shifting the shuttle valve. This 6 seconds, added to the 1.5 seconds duration which the on-timer was set, equals 7.5 seconds. Dividing 60 seconds by 7.5 equals eight cycles or breaths per minute. The knob 100 may be suitably calibrated to indicate the number of breaths per minute.

As another example, if the off-timer were set to attain the preselected pressure in 1.5 seconds, 20 breaths per minute would be provided (60 divided by 1.5 plus 1.5).

When the preset pressure for the off-timer chambers 40, 41 is attained, the shuttle valve will, of course, shift so that the control pressure is once more applied to the control line 20 for opening the demand valve, and the control pressure is once more applied to the on-timer chambers 44, 45. Meanwhile, the pressure in the off-timer chambers is quickly vented through the shuttle valve vent 218 so as to be ready for the next timing operation.

Based on the foregoing, it can be seen that great convenience and adjustability is provided by the controller. Further, all of the necessary functions are compactly packaged within a single control module. All controls are pneumatic and are conveniently operated by the gas pressure available for the patient. From the operator's standpoint, the connections to the demand valve are easily made, and the control module is conveniently located adjacent the patient for making the desired adjustments and observing the settings made. Also, the indicator conveniently tells the operator when gas is being applied to the patient.

Improved Demand Valve Assembly of FIGS. 21-24

The demand valve assembly 12 of FIG. 1 is, as indicated above, described in detail in U.S. Pat. No. 3,795,257. It includes a main valve through which the oxygen supply flows when it is open. When the valve is closed, the input oxygen pressure is applied to both sides of the valve, causing it to remain in a balanced, closed position. To open it, the pressure on the downstream side is reduced to create an unbalanced condition. This unbalanced condition is created utilizing a pilot valve that bleeds pressure from the downstream side of the main valve. The pilot valve is opened manually by depressing a button on the top of the valve, comparable to that shown at 228 in FIG. 17. The pilot valve is also openable in response to input breathing of the patient. A slight pressure reduction caused by the patient reacts against a sensitive pressure responsive diaphragm to open the pilot valve. The main valve, the pilot valve, as well as the manually-operated button for opening the pilot valve, are all contained within a subassembly which is identified as component 314 of a demand valve assembly 312, illustrated in FIG. 21, within the shell 18 of FIG. 1. The remaining components of the demand valve assembly of the type set forth in U.S. Pat. No. 3,795,257 are contained in an outlet subassembly 316, as shown in FIG. 21. That subassembly includes easily openable flap valves 318, partially shown in FIG. 21, that permit flow out of the valve assembly to the patient, but prevent flow from the patient upstream of that valve. The valve elements 318 cooperate with a valve seat 320 which is mounted on a flexible diaphragm 322. The valve seat 320, movable with the flexible diaphragm, also functions as an exhaust valve element that cooperates with an annular valve seat (not shown) in the outlet assembly 316. That exhaust valve will open to permit the patient to exhale to the exterior of the assembly 312.

In the form of the demand valve assembly shown in U.S. Pat. No. 3,795,257, the outlet subassembly 316 threadably connects to the main valve subassembly 314. However, in the improved form of the demand valve assembly 312 illustrated in FIG. 21, an additional subassembly 326 has been incorporated into the demand valve assembly between the main valve subassembly 314 and the outlet valve subassembly 316. As seen in FIGS. 24-24, this safety subassembly 326 includes a short cylindrical housing 328 that is threaded on one end to mate with the downstream threaded end 315 of the main valve subassembly 314, and is threaded on its other end to mate with the upstream end 317 of the outlet valve subassembly 316. The safety valve subassembly includes, within the housing 328, a signaling device 334 (FIG. 23) to warn the operator of the automatic ventilator that the oxygen is not reaching the patient, and an anti-suffocation valve 336 (FIG. 24) to permit the patient to breathe exterior air if insufficient air is reaching the patient from the ventilator oxygen supply. Those components are compactly positioned within the housing 328, while permitting oxygen to flow through the safety subassembly from the main valve subassembly to the outlet subassembly.

More specifically, the housing 328 includes a main, diametrically extending support strut 338 and side struts 339, 340 which define enlarged openings 341 through which oxygen can flow axially through the housing. These openings are made sufficiently large so that the main and outlet valve subassemblies are in unrestricted communication. The strut 338 includes a central passage 343 which extends axially and then radially to a ball-type check valve 347 (FIG. 24), including a ball 342 held against a valve seat 344 by a spring 346. The spring is mounted within a passage in the strut downstream of the valve seat 344 and held in position by an adjusting screw 348 mounted in the housing 328. A branch passage 352 in the side strut 340 downstream from the check valve ball 342 contains a whistle 354, or other such device which will produce an audible signal with sufficient gas flow through it. The outlet from the whistle opens into an axially thin but circumferentially wide slot 356 that opens to the exterior of the housing. The wide outlet minimizes the chance of blockage. The whistle is positioned within the passage in the housing by friction or other suitable means.

If oxygen is not reaching the patient because of some obstruction in the patient's windpipe or in the outlet of the demand valve assembly, the operator of the automatic ventilator should be warned of this. The continuing input of oxygen by way of the automatic ventilator will produce a pressure rise in the chamber formed by the housing 330, and at a predetermined level, this increased pressure will cause the ball 342 of the check valve to move to an open position so that excess oxygen is vented from the chamber through the whistle. The flow of this oxygen through the whistle provides the warning signal to the operator.

The anti-suffocation valve 336 includes a wide, flat inlet passage 370 which extends from the exterior of the housing inwardly towards the center of the housing. The wide passage minimizes the risk of blockage. An air inlet 372 branches from that passage to form an anti-suffocation valve inlet through a wall of the strut 338 that opens into the chamber formed by the housing 328. A flexible, somewhat mushroom-shaped valve member 374 includes a flat, flexible valve portion 374a that permits flow into the housing but prevents flow out of the housing. The valve member 374 is captured within the housing by virtue of a stem 374b extending through a hole in the strut wall. The anti-suffocation valve is normally closed. However, if the patient creates a sufficient pressure reduction in the safety housing as a result of not being able to obtain sufficient oxygen through the main valve subassembly, the valve member 374a will move to the dotted line position indicated in FIG. 24, thus allowing exterior air to flow into the patient, as indicated by the arrows in that FIG. There are a large number of demand valve assemblies made in accordance with U.S. Pat. No. 3,795,257 currently being used. The compact safety subassembly 328 may be added to those demand valve assemblies in the field, by merely unthreading the main valve subassembly 314 from the outlet valve subassembly 316, and inserting and threadably connecting the safety subassembly 328. Of course, this same assembly technique is useful for new production as well.

Thus, it can be seen that the safety subassembly represents a valuable improvement and addition to the automatic ventilator system. Resuscitation efforts with the automatic ventilator are much more effective and reliable than manual resuscitation techniques. Further, the operator is warned if the patient is not receiving adequate oxygen with the patient demand valve being automatically cycled by the ventilator control, and can then take necessary corrective action. Further, if the patient is not receiving sufficient oxygen through the automatic ventilation technique, supplementary external air is available through the anti-suffocation valve. This feature provides a desirable function for the demand valve assembly, whether it is operated manually or operated automatically by the control module. The safety subassembly provides these additional features without interfering with the normal critical operation of the patient subassembly.

What is claimed is:

1. An automatic ventilator system, comprising:
   a demand valve assembly for supplying gas to a patient which includes a supply gas inlet and an inlet valve which will open in response to the patient's inhaling breathing demands, said assembly further including an exhaust valve which will open in response to the patient's exhaling demands; and
   a pneumatic controller providing a control pressure to open said inlet valve for a predetermined period of time and at predetermined intervals to provide automatically a measured quantity of gas through the demand valve assembly to the patient at desired intervals, said control pressure being provided by said controller independently of said inhaling and exhaling demands, and said inlet valve being operable by patient inhaling demands independently of said control pressure.

2. The system of claim 1, wherein said controller includes a pneumatic on-timer for controlling the length of time the control pressure is provided to said demand valve assembly and a pneumatic off-timer controlling the length of time said control pressure is not provided to said demand valve assembly.

3. The system of claim 2, wherein said on-timer has a flow control valve open to said control pressure and an on-timer chamber receiving gas through said flow control valve to establish a sensing pressure for determining the length of time said control pressure is provided to said demand valve assembly, said off-timer including a flow control valve and an off-timer chamber receiving gas through said off-timer control valve to establish a sensing pressure for determining the length of time said control pressure is not provided to said demand valve assembly, and said controller includes a shuttle valve having an off-timer vent for venting the pressure in said off-timer chamber when a control pressure is to be provided to said demand valve assembly, and said shuttle valve having an on-timer vent for venting said on-timer chamber when said control pressure is not to be provided to said demand valve assembly.

4. The system of claim 3, including a gas supply line leading to said demand valve assembly, and a tidal volume control valve in said supply line to control the volume of gas to the patient when said demand valve assembly is open.

5. The system of claim 3, wherein said shuttle valve has an inlet for connection to a gas supply, a control gas outlet and a control line connected between said outlet and said demand valve assembly, said shuttle valve including a pressure responsive control member which is shiftable between an ON position wherein said inlet is open to said outlet and an OFF position wherein said inlet is closed to said outlet, said on-timer flow control valve being open to said shuttle valve outlet, and a sensing pressure line connecting said on-timer chamber to said shuttle valve to shift the shuttle valve control member from its ON position to its OFF position when the pressure in said on-timer chamber reaches a predetermined level, said shuttle valve including a second outlet leading to said off-timer flow control valve to direct inlet gas to said off-timer valve when said shuttle valve control member is in its OFF position and a sensing pressure line connecting said off-timer chamber to said shuttle valve to shift said shuttle valve control member from its OFF position to its ON position, said shuttle valve venting the pressure in said off-timer chamber when said shuttle valve is in its ON position and venting said on-timer chamber when said shuttle valve is in its OFF position.

6. The system of claim 3, wherein said off-timer flow control valve is adjustable so as to vary the time necessary to raise the pressure in the off-timer chamber to a level to cause said shuttle valve to switch from OFF to ON, thereby controlling the frequency of the ON periods.

7. The system of claim 3, wherein said on-timer flow control valve is adjustable so that the time interval required to raise the pressure in the ton-timer chamber to a level to shift said shuttle valve to its OFF position, which thereby controls the volume of gas supplied to the patient during the interval of time in which the shuttle valve is in its ON position.

8. The system of claim 3, wherein said timer flow control valves are connected to said shuttle valve vents so that said timing chambers vent through their respective timer flow control valves in their venting modes.

9. An automatic ventilator system, comprising:
a demand valve for supplying gas to a patient in response to the patient's breathing demands; and
a pneumatic controller providing a control pressure to open said valve to a predetermined period of time and at predetermined intervals to provide automatically a measured quantity of gas through the valve to the patietn at desired intervals; said controller including a pneumatic on-timer for controlling the length of time the control pressure is provided to said demand valve, and a pneumatic off-timer controlling the length of time said control pressure is not provided to said demand valve, said on-timer has a flow control valve open to said control pressure and an on-timer chamber receiving gas through said flow control valve to establish a sensing pressure for determining the length of time said control pressure is provided to said demand valve, said off-timer including a flow control valve and an off-timer chamber receiving gas through said off-timer control valve to establish a sensing pressure for determining the length of time said control pressure is not provided to said demand valve, and said controller includes a shuttle valve having an off-timer vent for venting the pressure in said off-timer chamber when a control pressure is to be provided to said demand valve, and said shuttle valve having an on-timer vent for venting said on-timer when said control pressure is not to be provided to said demand valve;
said controller including a check valve connected in parallel to the connection between each timer flow control valve and its timing chamber to permit said timing chambers to quickly vent through the check valves and their respective flow control valves to said shuttle valve when in their respective venting modes.

10. The system of claim 9, wherein said check valves are physically incorporated into their respective flow control valve structures.

11. The system of claim 1, wherein said demand valve assembly includes an element to manually operate said valve assembly and provide gas to the patient, and a piston pneumatically operating said element in response to said control pressure.

12. The system of claim 11, including an indicator operated by said control pressure when said demand valve assembly is opened to provide a visual indication that the patient is receiving gas through said demand valve assembly.

13. The system of claim 11, including a gas supply line connected to said demand valve assembly, and an adjustable tidal volume flow control valve in said supply line to adjust the flow of gas to the patient when said demand valve assembly is open.

14. The system of claim 1, wherein said demand valve assembly is part of an assembly which further includes an anti-suffocation valve which permits the patient to breathe ambient air if a sufficient amount of gas is not being provided under the control of said controller.

15. The system of claim 1, including a signaling device connected to said demand valve assembly to provide an audible signal if the gas flow to the patient from the demand valve assembly is blocked.

16. The system of claim 15, wherein said signaling device is responsive to the pressure in said demand valve assembly to provide said signal at a predetermined pressure.

17. The system of claim 15, wherein said demand valve assembly includes a main valve subassembly, an outlet valve subassembly and a safety subassembly which is positioned between said main and outlet subassemblies, with said safety subassembly including said signaling device and an anti-suffocation valve which permits ambient air to be drawn into said demand valve assembly when an insufficient supply of said gas is being received by the patient.

18. An automatic ventilator system for providing desired volumes of oxygen or other gas to a patient at desired intervals, comprising:
   a demand valve assembly for connection to a gas line for supplying gas to a patient in response to the patient's breathing, said assembly including (1) an inlet valve which opens in response to the patient's inhaling pressure reduction (2) a manually operable control element for opening said inlet valve, and (3) an exhaust valve which opens in response to the patient's exhaling pressure; and
   a pneumatic controller for operating said valve assembly by means other than in response to the patient's breathing to permit a measured quantity of gas to flow through said gas line and said valve assembly to the patient at desired intervals, said controller including:
   a shuttle valve having an inlet for connection to a gas supply and a control pressure outlet leading to said demand valve assembly to provide a control pressure for operating said demand valve assembly and a pressure responsive control member which is shiftable between an ON position wherein said inlet is open to said outlet and an OFF position wherein said inlet is closed to said outlet;
   a pneumatic on-timer for controlling the length of time the shuttle valve control member is in its ON position, said on-timer having a flow control valve open to said shuttle valve outlet and an on-timer chamber receiving gas through said flow control valve, and a sensing pressure line connecting said chamber to said shuttle valve to shift the shuttle valve control member from its ON position to its OFF position when the pressure in said chamber reaches a predetermined level;
   a pneumatic off-timer for controlling the length of time the shuttle valve is in its OFF position, said off-timer including a flow control valve, said shuttle valve including a second outlet leading to said off-timer flow control valve, said shuttle valve control member directing inlet gas to said off-timer flow control valve when said shuttle valve control member is in said OFF position, said off-timer further including an off-timer chamber receiving gas through said off-timer control valve, and a sensing pressure line connecting said off-timer chamber to said shuttle valve to shift said shuttle valve control member from its OFF position to its ON position at a predetermined pressure level;
   said shuttle valve having an off-timer chamber vent for venting the pressure in said off-timer chamber when said shuttle valve is in its OFF position.

19. The system of claim 18, including a tidal volume control valve connected to said demand valve assembly to control the volume of gas to the patient when said demand valve assembly is being held in an open position by said controller.

20. The system of claim 18, wherein said off timer flow control valve is adjustable so as to vary the time necessary to raise the pressure in the off-timer chamber to a level to cause said shuttle valve to switch from OFF to ON, thereby controlling the frequency of the ON periods.

21. The system of claim 20, wherein said on-timer flow control valve is adjustable so that the time interval required to raise the pressure in the on-timer chamber to a level to shift said shuttle valve to its OFF position which thereby controls the time in which the demand valve assembly is held in its open position by said controller.

22. An automatic ventilator system for providing desired volume of oxygen or other gas to a patient at desired intervals, comprising:
   a demand valve to connection to a gas line for supplying gas to a patient in response to the patient's breathing; and
   a pneumatic controller for operating said valve assembly by means other than in response to the patient's breathing to provide automatically a measured quantity of gas through said valve to the patient at desired intervals, said controller including:
   a shuttle valve having an inlet for connection to a gas supply and a control pressure outlet leading to said demand valve to provide a control pressure for operating said demand valve and a pressure responsive control member which is shiftable between an ON position wherein said inlet is open to said outlet and an OFF position wherein said inlet is closed to said outlet;
   a pneumatic on-timer for controlling the length of time the shuttle valve control member is in its ON position, said on-timer having a flow control valve open to said shuttle valve outlet and an on-timer chamber receiving gas through said flow control valve, and a sensing pressure line connecting said chamber to said shuttle valve to shift the shuttle valve control member from its ON position to its OFF position when the pressure in said chamber reaches a predetermined level;
   a pneumatic off-timer for controlling the length of time the shuttle valve is in its OFF position, said off-timer including a flow control valve, said shuttle valve including a second outlet leading to said off-timer flow control valve, said shuttle valve control member directing inlet gas to said off-timer flow control valve when said shuttle valve control member is in said OFF position, said off-timer further including an off-timer chamber receiving gas through said off-timer control valve, and a sensing pressure line connecting said off-timer chamber to said shuttle valve to shift said shuttle valve control member from its OFF position to its ON position at a predetermined pressure level;
   said shuttle valve having an off-timer chamber vent for venting the pressure in said off-timer chamber when said shuttle valve is in its off position;

said timer flow control valves being connected to said shuttle valve vents so that said timing chambers vent through their respective timer flow control valves in their venting modes.

23. An automatic ventilator system for providing desired volumes of oxygen or other gas to a patient at desired intervals, comprising:
a demand valve for connection to a gas line for supplying gas to a patient in response to the patient's breathing; and
a pneumatic controller for operating said valve assembly by means other than in response to the patient's breathing to provide automatically a measured quantity of as through said valve to the patient at desired intervals, said controller including:
a shuttle valve having an inlet for connection to a gas supply and a control pressure outlet leading to said demand valve to provide a control pressure for operating said demand valve and a pressure responsive control member which is shiftable between an ON position wherein said inlet is open to said outlet and an OFF position wherein said inlet is closed to said outlet;
a pneumatic on-timer for controlling the length of time the shuttle valve control member is in its ON position, said on-timer having a flow control valve open to said shuttle valve outlet and an on-timer chamber receiving gas through said flow control valve, and a sensing pressure line connecting said chamber to said shuttle valve to shift the shuttle valve control member from its ON position to its OFF position when the pressure in said chamber reaches a predetermined level;
a pneumatic off-timer for controlling the length of time the shuttle valve is in its OFF position, said off-timer including a flow control valve, said shuttle valve including a second outlet leading to said off-timer flow control valve, said shuttle valve control member directing inlet gas to said off-timer flow control valve when said shuttle valve control member is in said OFF position, said off-timer further including an off-timer chamber receiving gas through said off-timer control valve, and a sensing pressure line connecting said off-timer chamber to said shuttle valve to shift said shuttle valve control member from its OFF position to its ON position at a predetermined pressure level;
said shuttle valve having an off-timer chamber vent for venting the pressure in said off-timer chamber when said shuttle valve is in its OFF position, and
check valves each respectively connected in parallel to the connection between the timer flow control valve and its timing chamber to permit said timing chambers to quickly vent through their respective flow control valves to said shuttle valve when in their respective venting modes and bypass metered flow through said timer flow control valve.

24. The system of claim 23, wherein said check valves are physically incorporated into their respective flow control valve structures.

25. The system of claim 18, including a pneumatically operated piston for pneumatically operating said element in response to said control pressure.

26. The system of claim 25, including an indicator responsive to said control pressure when said demand valve assembly is open to provide a visual indication when the patient is receiving gas through said demand valve assembly.

27. The system of claim 18, wherein said controller includes a gas inlet, a supply gas outlet and a passage from said inlet bypassing said shuttle valve and leading to said controller supply gas outlet, said supply gas line extending from said supply outlet to said demand valve assembly and a tidal volume flow control valve in said passage to control the volume of gas to the patient when the demand valve assembly is open.

28. An automatic ventilator system for providing desired volume of oxygen or other gas to a patient at desired intervals, comprising:
a demand valve for supplying gas to a patient in response to the patient's breathing;
a pneumatic controller for operating said valve by means other than in response to the patient's breathing to provide automatically a measured quantity of gas to the patient at desired intervals, said controller including a housing having a supply gas inlet, a supply gas outlet for connection to said demand valve, a control gas outlet for connection to said demand valve to control the opening of said demand valve by means other than the patient's breathing, and a passage formed in a lower surface of said housing leading from said inlet to said supply gas outlet;
a tidal volume flow control valve in said housing to control flow through said passage to said supply gas outlet;
a pneumatic timer in said housing for providing a control gas pressure to said control gas outlet to open said demand valve for a predetermined time at predetermined intervals;
said housing further having a timer gas passage in said lower surface connecting said inlet to said timer;
a control passage in said lower surface connected to said control gas outlet; and
a plate secured to said lower surface to complete said passages.

29. The system of claim 28, including a shuttle valve in said housing and in communication in said housing with said timer gas passage and having an outlet in communication with said control passage, said pneumatic timer including an on-timer in said housing which measures the period of time control gas is applied through said control passage to said demand valve, and an off-timer in said housing for measuring the period of time control gas is not applied through said control passage to said demand valve.

30. The system of claim 29, wherein said shuttle valve has vent passages in said housing for venting a gas from said timers.

31. The system of claim 29, wherein said on-timer includes a flow control valve in said housing in communication with said control passage, an on-timer chamber in said housing, a passage in the bottom of said housing extending between said flow valve in said chamber and a passage in the bottom of said housing extending between said chamber and said shuttle valve so that the pressure in said chamber is sensed by said shuttle valve.

32. The system of claim 29, wherein said off-timer includes a flow control valve in said housing, a passage in the lower surface of said housing connecting an outlet in said shuttle valve to said off-timer flow control valve, an off-timer chamber in said housing, a passage in the lower surface of said housing interconnecting said off-timer flow control valve and said off-timer chamber and a passage in the lower surface of said housing connecting said off-timer chamber to one of said vent passages, said passages being completed by said plate secured to the lower surface of the housing.

33. The system of claim 28, including a pressure regulator in said housing in communication with said passage leading from said inlet to said supply gas outlet and in communication with said timer gas passage connecting said inlet to said timer, whereby both the supply gas to said demand valve and the control gas to the demand valve are maintained at a desired regulated pressure, said pressure regulator and said tidal volume flow valve being physically close to said supply gas outlet.

34. The system of claim 28, wherein said housing has a generally rectangular configuration, and said flow control valves are arranged diagonally in a row within said housing, each of said flow control valves including a rotatable central core which terminates adjacent an upper surface of said housing in position to receive a manual control knob, if desired, for each of said flow control valves.

35. A demand valve assembly for use with resuscitation equipment, comprising:
a main valve subassembly for connection to a source of breathable gas and including a housing;
an outlet valve subassembly for connection to a patient and including a housing; and
a safety subassembly including a housing positioned between and connected to said main subassembly and said outlet subassembly housings, said safety subassembly including a device for signaling when the pressure within the demand valve assembly exceeds a predetermined maximum, and including an anti-suffocation valve to permit the flow of ambient air into the demand valve assembly when pressure reduction produced by the patient's breathing demands reaches a predetermined level.

36. The assembly of claim 35, wherein said signaling device incorporates a whistle which produces an audible sound when said maximum is reached, and said anti-suffocation valve is a pressure-responsive one-way valve.

37. The assembly of claim 35 wherein said safety subassembly housing is generally cylindrical having a plurality of struts extending across said safety subassembly housing an forming one or more enlarged openings, permitting gas flow through said safety subassembly housing, said signalling device and said anti-suffocation valve being mounted on said struts.

38. A method of automatically providing a predetermined volume of gas to a patient during a predetermined interval at a predetermined frequency, comprising the steps of:
applying breathable gas to a patient through a demand valve assembly which permits flow to a patient in response to the patient's inhalation pressure reduction, and permits exhalation of gas in response to the patient's exhalation pressure;
applying control gas through an on-timer flow control valve to an on-timer chamber;
utilizing the pressure in said chamber as an indication of the time in which flow of said breathable gas through said demand valve assembly is permitted by interrupting the flow of breathable gas to the patient through said demand valve assembly in response to a predetermined pressure in said chamber;
applying gas through an off-timer flow control valve to an off-timer chamber; and
utilizing the pressure in said off-timer chamber as an indication of the time in which the flow to the patient is interrupted by opening said demand valve assembly in response to a predetermined pressure attained in said off-timer chamber.

39. A method of automatically providing a predetermined volume of gas to a patient during a predetermined interval and at a predetermined frequency, comprising the steps of:
applying breathable gas to a patient demand valve assembly which permits flow to a patient in response to the patient's inhalation pressure reduction, and permits exhalation of gas in response to the patient's exhalation pressure;
applying a control gas pressure to said assembly to hold the demand valve assembly open;
applying said control gas through an on-timer flow control valve to an on-timer chamber; and
venting said control gas pressure in response to a predetermined pressure in said chamber, and thereby allow the demand valve assembly to close and interrupt the flow of said breathable gas to the patient.

40. The method of claim 39, including:
supplying control gas through an off-timer flow control valve to an off-timer chamber; and
permitting said control gas pressure to be applied to said demand valve in response to a predetermined pressure in said off-timer chamber.

41. The method of claim 39, including the step of conducting said breathable gas through an adjustable tidal volume flow control valve to determine the volume of gas conducted to said patient when the demand valve assembly is open.

42. The method of claim 39, including the step of providing an audible signal in response to a predetermined pressure in said demand valve assembly which signals blockage of the flow of said breathable gas to the patient.

43. The method of claim 42, wherein said signal-providing step includes permitting breathable gas flow out of said demand valve assembly through a whistle which provides said signal.

44. A system for providing breathable gas to a patient, comprising:
a demand valve assembly for supplying breathing gas to a patient in response to the patient's breathing demands, said demand valve assembly including (1) an inlet valve to permitting the flow of breathable air to the patient in response to said patient's inhalation pressure reduction, (2) an outlet valve responsive to the patient's exhalation pressure, and (3) a manually operable element for opening said inlet valve to permit breathable supply gas to flow to the patient;
a shell to fit over said demand valve assembly, said shell supporting a member for operating said element in response to a control pressure; and
a controller for providing said control pressure to said member for automatically cycling the opening and closing of said inlet valve.

45. The system of claim 44, wherein said control gas pressure is provided through a control line extending between said controller and said shell.

46. The system of claim 45, wherein said controller includes a breathable gas inlet, a tidal volume flow control valve connected in series with said gas inlet and a breathable gas outlet, a gas line extending between said controller breathable gas outlet and a gas inlet in said demand valve assembly in parallel with said control pressure line.

47. The system of claim 46, wherein said controller includes means connected to said controller gas inlet for providing periodic control pressures to said control pressure line.

* * * * *